United States Patent [19]

Heaven

[11] Patent Number: 5,306,245
[45] Date of Patent: Apr. 26, 1994

[54] ARTICULATING DEVICE

[75] Inventor: Malcolm D. Heaven, Hopewell, N.J.

[73] Assignee: Advanced Surgical Inc., Princeton, N.J.

[21] Appl. No.: 21,456

[22] Filed: Feb. 23, 1993

[51] Int. Cl.⁵ .............................................. A61M 37/00
[52] U.S. Cl. ........................................ 604/95; 604/280
[58] Field of Search ................. 604/95, 53, 280–282; 128/656, 657, 658, 344, 772; 606/194

[56] References Cited

U.S. PATENT DOCUMENTS

| | | |
|---|---|---|
| 2,498,692 | 2/1950 | Mains . |
| 3,044,461 | 7/1962 | Murdock . |
| 3,162,214 | 12/1964 | Bazinet, Jr. . |
| 3,266,059 | 8/1966 | Stelle . |
| 3,470,876 | 10/1969 | Barchilon . |
| 3,669,098 | 6/1972 | Takahashi . |
| 4,150,676 | 4/1979 | Jackson . |
| 4,245,624 | 1/1981 | Komiya . |
| 4,329,983 | 5/1982 | Fletcher . |
| 4,353,358 | 10/1982 | Emerson . |
| 4,586,923 | 5/1986 | Gould et al. . |
| 4,589,410 | 5/1986 | Miller . |
| 4,643,720 | 2/1987 | Lanciano . |
| 4,898,577 | 2/1990 | Badger et al. . |
| 5,114,402 | 5/1992 | McCoy ................................ 604/95 |
| 5,231,989 | 8/1993 | Middeleman et al. ............ 604/95 X |
| 5,255,668 | 10/1993 | Umeda ............................ 604/282 X |

Primary Examiner—John D. Yasko
Attorney, Agent, or Firm—Burns, Doane, Swecker & Mathis

[57] ABSTRACT

A uniplanar medical steering device which includes a tubular member of a material such as stainless steel, a hinge formed by a cut-out in a wall of the tubular member and a control wire for bending a first end of the tubular member back and forth in a plane towards and away from a second end of the tubular member. A medical device such as a catheter can be provided within the tubular member and an outer member surrounding the tubular member can be used to cover the cut-out. The steering device allows accurate positioning of a medical device and prevents twisting of the medical device when bent by the control wire.

16 Claims, 2 Drawing Sheets

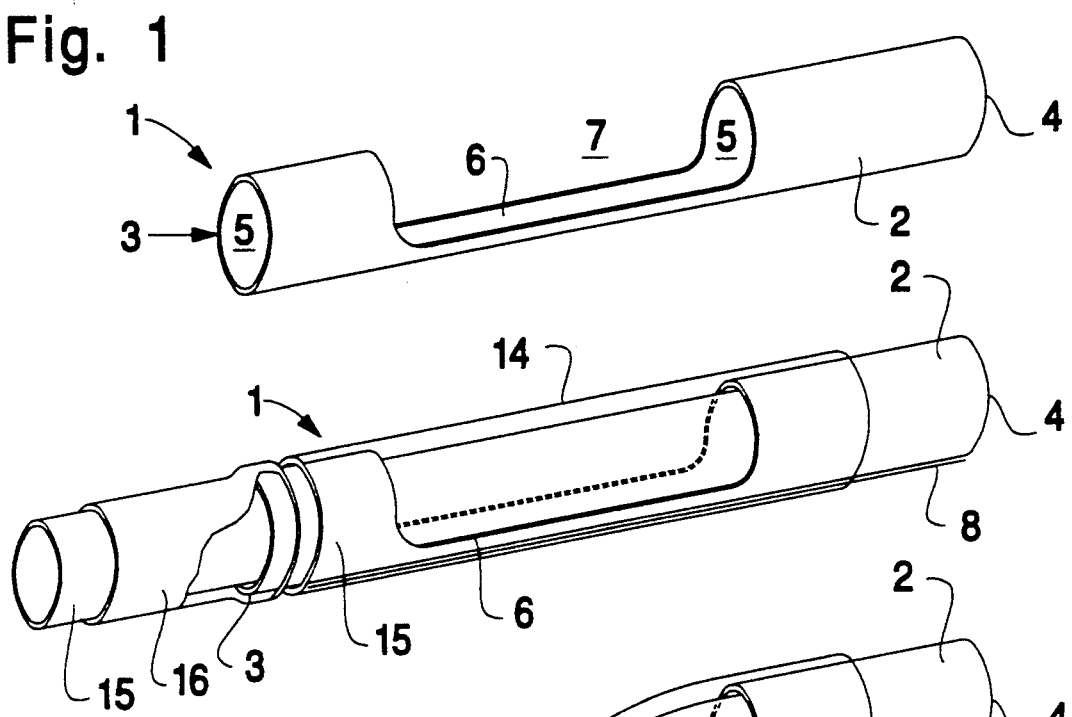
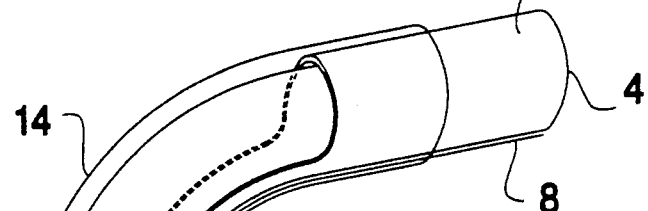
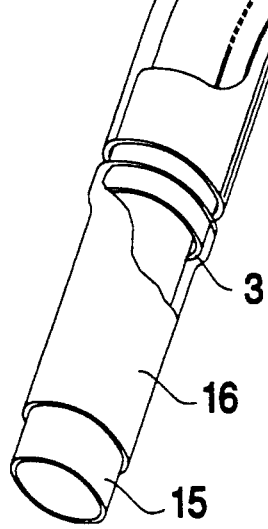

ARTICULATING DEVICE

BACKGROUND OF THE INVENTION

1. Field of the Invention

The invention relates to an articulating device and method of manufacture thereof. In addition, the invention relates to the use of the articulating device for steering medical devices such as the distal portion of medical devices typically used in minimally invasive surgery.

2. Description of Related Art

Rigid instruments, which may, for example, be catheters, graspers, or other tools, limit the ability of the surgeon to access the interior portions of the body. By having articulateable distal portions this adds an extra degree of freedom, thus reducing the need for changing tools during a procedure, and as a result reducing the time needed for the procedure to the mutual benefit of surgeon and patient alike.

As already stated the majority of tools used in these procedures are rigid. There are a variety of devices which have a degree of steerability added via a fixed curve being introduced in the distal end, and some devices which have steerable tips. Examples of steerable tips can be found in commonly owned and copending application Ser. No. 07/903,587 and U.S. Pat. No. 4,934,340 ("Wendel"), and U.S. Pat. No. 5,114,403 ("Clarke"). In many of these devices the distal tip, on being articulated, suffers from a problem commonly described as "S-ing". This term refers to the tendency for the articulating portion of the device to take on an S-shape, in which it no longer lies in a single plane. This is particularly problematical in small diameter devices wherein it is not possible to add stiffening members to alleviate this. The current invention offers a means of producing small diameter devices which freely articulate but have no tendency to "S". Additionally, for the aforementioned types of surgical devices it is frequently highly desirable that the tip be able to support significant end loading in the bent (or articulated) state. Existing devices generally do not provide such strength.

Various devices are known for steering medical devices such as catheters. For instance, steering mechanisms are discussed in U.S. Pat. Nos. 4,353,358 ("Emerson"); 3,470,876 ("Barchilon") and 4,245,624 ("Komiya").

U.S. Pat. No. 4,353,358 ("Emerson") discloses a disposable sigmoidoscope having a tubular portion of plastic material wherein a free end is weakened by providing one or more cut-outs or notches or by making the side of the tubular portion thinner. An operator cord member of wire, plastic or string member is attached to the free end and extends along the outer surface of the segments between the cut-outs, on the inside of the segments or through the weakened side of the device. Pulling on the member allows the tubular member to be bent somewhat but not so much that the operator can no longer see through the passage through the tubular member. A protective outer layer or sheath covers the cut-outs in order to prevent discomfort to the patient during insertion and withdrawal of the device and prevent material from entering the device through the cut-outs.

U.S. Pat. No. 3,470,876 ("Barchilon") discloses a ½ to 2 inch diameter catheter including an outer tube, an inner tube and a rigid end piece connecting the distal ends of the inner and outer tubes. The end piece has a flange and four tensioning cords are attached thereto such that each cord is offset 90° with respect to each other. The inner and outer tubes are of flexible material such as a silicone compound having a durometer of 48. The cords are of material such as wire or nylon and the catheter can be bent in any desired direction by pulling on one or more of the cords.

U.S. Pat. No. 4,245,624 ("Komiya") discloses an endoscope having an observation optical system, a flexible plastic guide tube and a wire, each of which is located in a respective one of three channels extending longitudinally through a distal end of the endoscope. The guide tube is movable longitudinally beyond the distal end of the endoscope and the wire is attached to a distal end of the guide tube for bending the guide tube. When the guide tube is empty, liquid can be sprayed from or sucked into the distal end thereof. On the other hand, a medical implement such as forceps can be inserted into the guide tube and the wire can be used to bend the guide tube and medical implement toward a prescribed location in a body cavity. The guide tube can be made more flexible by using a plastic material foamed at a progressively higher rate at the distal end thereof. Alternatively, the guide tube can be made thinner at the distal end thereof or the guide tube can be surrounded by a coil of plastic or metal which has a progressively larger pitch toward the distal end of the guide tube.

It would be desirable in the medical field to have a steering device which prevents S-ing and instead allows accurate uniplanar bending of a distal end of a medical device. It is further desirable that such a steering device be capable of sustaining significant end-loading forces in the articulated state.

SUMMARY OF THE INVENTION

The invention provides a medical uniplanar steering device which includes a tubular member, hinge means and articulating means. The tubular member has first and second spaced-apart ends and a central passage extending axially between the first and second ends. The hinge means connects the first end to the second end and permits uniplanar bending of the first end back and forth in a plane towards and away from the second end. The hinge means comprises a cut-out in a wall of the tubular member. The articulating means moves the first end in the plane towards the second end of the tubular member. The articulating means comprises a control wire located on a side of the tubular member opposite to a side of the tubular member in which the cut-out is located.

According to various features of the invention, the control wire can be attached to the first end of the tubular member such that it extends along and beyond the second end of the tubular member and causes the first end to bend towards the second end when tension is applied to the control wire. For instance, the control wire can be located on an outer periphery of the tubular member.

The tubular member can have a circular cross section which is substantially uniform in diameter from the first end to the second end. In a preferred embodiment, the tubular member comprises a stainless steel tube. However, any suitable material can be used for the tubular member.

The hinge means can be defined by a circumferential section of the tubular member which generally extends no more than ¼ of the circumferential distance around the tubular member. The cut-out can extend a distance along the tubular member which is greater than the circumferential distance around the tubular member. The cut-out can extend circumferentially more than half way around the tubular member and can be defined by two spaced-apart longitudinally extending side edges which are parallel to each other and parallel to a central axis of the tubular member. Alternatively, the side edges can lie in a plane which is non-parallel to the central axis of the tubular member. For instance, the cut-out can be tapered such that the cut-out is larger at an end thereof closest to the first end of the tubular member. The cut-out can be defined by two axially spaced-apart end edges of the wall wherein the end edges lie in planes which are parallel to each other. The end edges can be joined to the side edges by arcuate corner edges in the wall of the tubular member.

A medical device can be provided within the tubular member such that a distal end of the medical device extends beyond the first end of the tubular member. The distal end of the medical device can thus be oriented in a desired direction by the control wire. The medical device can comprise a catheter within the tubular member and the catheter can include a balloon at a distal end of the catheter extending beyond the first end of the tubular member. The device can include an outer member surrounding the tubular member such that the outer member completely covers the cut-out.

BRIEF DESCRIPTION OF THE DRAWINGS

FIG. 1 shows a tubular member of a medical uniplanar steering device in accordance with the invention;

FIG. 2 shows a medical uniplanar steering device in accordance with the invention wherein the steering device is in a non-bent condition;

FIG. 3 shows the device of FIG. 2 in a bent condition; and

DETAILED DESCRIPTION OF THE INVENTION

Figure 4:
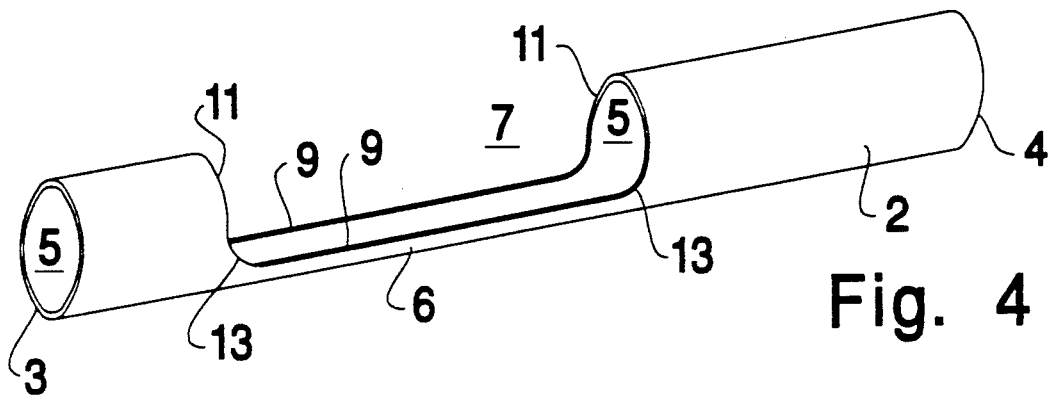
FIGS. 4-6 show different embodiments of the tubular member in accordance with the invention.

The invention offers considerable improvement over existing medical steering devices. In particular, the medical steering device of the invention allows accurate uniplanar bending of a medical device associated with or made part of the steering device.

The steering device of the invention includes a tubular section, such as, but not limited to, a stainless steel hypotube. The hypotube has a portion of its wall removed or ground away over a short distance. For instance, the angle of grind may be varied to give a progressive increase in material removal. In this way a range of flexibilities and/or range of curvature on articulating may be achieved. It has further been found, surprisingly, that the structure described has the additional benefit of being significantly superior to prior devices in that it resists the tendency to prolapse when end-loaded in the curved state. It is important that the side walls of the hypotube not be ground away entirely, as the curved cross-section contributes significant strength in resisting flexing in the transverse direction. The usefulness of the invention may be best described via a specific embodiment such as, but not limited to, a cholangiography catheter. The invention will be described in more detail by reference to the drawings.

Referring now to the drawings in detail, reference number 1 of FIG. 2 refers to a steering device according to the present invention. The device 1 has a tubular member 2, best illustrated by FIG. 1, having a first end 3 and a second end 4 with a central opening or passage 5 extending axially between first and second ends. The tubular member 2 preferably is circular in cross section and has a uniform diameter from the first end 3 to the second end 4. The tubular member 2 may be constructed of a variety of materials, such as plastic or metallic materials. However, the most preferable material is a biocompatible material such as a stainless steel alloy which is relatively durable, flexible and easily manufactured at a relatively low cost. It is also within the scope of the invention to use shape memory alloys which exhibit pseudo elastic, superelastic behavior to provide a high degree of flexibility for tubular member 2.

The second end 4 of the tubular member 2 may be connected to or form part of a rearwardly extending tubular portion located on the inner or outer periphery of the tubular member 2. The passage 5 can be used to accommodate or house a medical implement, such as a light source, forceps, catheter, graspers for arthroscopic procedures, scissors or other devices used, for example, in laparoscopic procedures. In use, the device 1 can be introduced into a body cavity by any conventional surgical procedure.

The tubular member 2 is constructed to enable the device 1 to bend so as to negotiate curvatures in body cavities. The first end 3 may be bent towards the second end 4 by means of a hinge 6 located between the first end 3 and the second end 4. The hinge 6 is provided by removal of a portion of the tubular member 2 whereby a cut-out 7 is provided in the tubular member 2. The hinge 6 can comprise a circumferential portion of the tubular member 2 which extends more than one-fourth around the circumference of the tubular member 2. According to the invention, the cut-out 7 preferably extends more than halfway around the circumference of the tubular member 2.

The hinge means 6 of the present invention provides numerous advantages over the prior art. In particular, the hinge means 6 enables uniplanar bending of the first end 3 back and forth in a plane towards and away from the second end 4. Accordingly, the steering device of the invention can avoid bending sideways or skewing out of a single plane. Moreover, the device of the present invention can articulate reliably and resist deformation due to its strength, even when end loaded or loaded sideways.

Referring now to FIG. 2, other elements which can be used with or incorporated in the medical steering device 1 can be seen. An operator cord member or articulating means 8, composed of metallic, plastic or cellulosic materials, is attached to a portion of the tubular member 2 adjacent to the first end 3 of the device. Preferably, the articulating means 8 is composed of metal, such as a wire. However, the articulating means 8 may also include combinations of the above-mentioned materials, such as a wire coated with plastic or polymeric materials.

The articulating means 8 extends longitudinally along the tubular member 2 from the first end 3 towards the second end 4. In a preferred embodiment, the articulating means 8 extends longitudinally along the outer surface of the tubular member 2, it is within the scope of the invention to have the articulating means extend partially or completely on the inside of the tubular member 2 or even partially or completely through the tubular member. The wire 8 is preferably located on the outside of the tubular member 2 so as to avoid interfering with the operation of medical implements inserted in the tubular member 2.

The articulating means 8 extends along the length of the tubular member 2 towards or beyond the second end 4 where it can be attached to an operator member such as a pull ring, trigger, handle, etc. The articulating means 8 may be attached to the first end 3 of the tubular member 2 by any suitable means, such as through a borehole in the tubular member 2, or by welding, brazing or riveting or by chemical/heat bonding. The articulating means 8 is preferably located on the same side of the tubular member 2 on which the hinge 6 is located. As such, this configuration allows uniplanar bending of the steering device 1.

Upon tensioning of the articulating means 8, the tubular member 2 bends at the location of the hinge means 6, as shown in FIG. 3. This allows the device 1 to, therefore, more easily follow the shape of the body cavity into which the device is inserted or perform work such as removing tissue with a medical tool associated with the steering device 1. Since many body cavities are serpentine in shape, it is highly desirable to be able to guide the medical steering device around corners as easily as possible, and this is greatly facilitated by the ability of the distal end 3 of the device 1 to be able to be bent under control of the operator during insertion. It is understood that bending the articulating device of the invention in, for example, an arthroscopic or laparoscopic procedure will allow the device to more easily access body portions.

Figure 5:
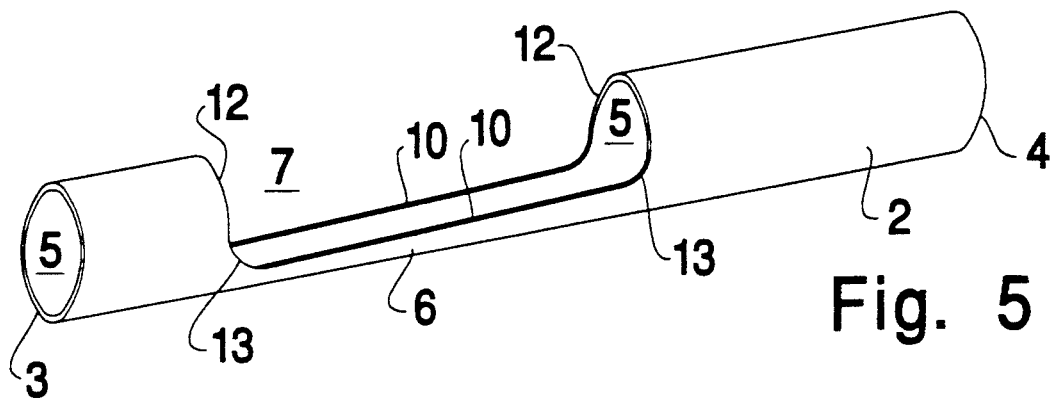
Figure 6:
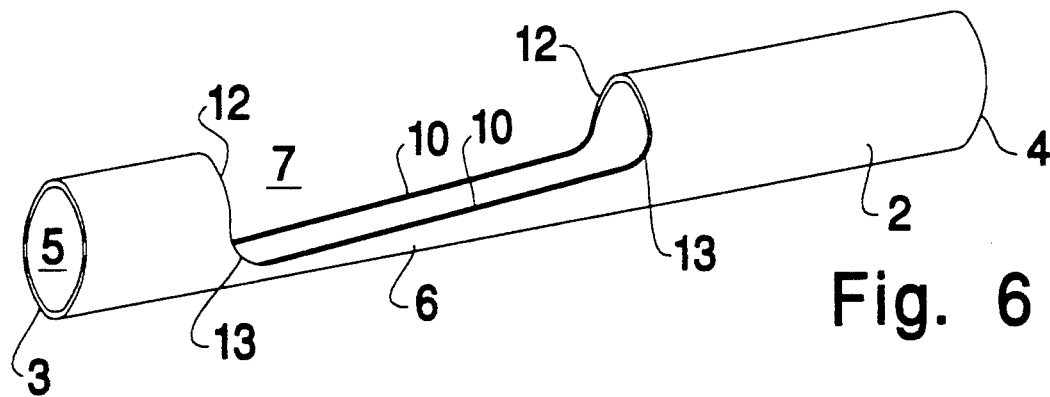

The hinge means 6 may be designed differently depending on the flexibility and strength desired. FIGS. 4–6 illustrate various configurations that may be utilized. In FIG. 4, the cut-out 7 of the tubular member is defined by two spaced-apart longitudinally extending side edges 9 of the wall of the tubular member 2, the side edges being parallel to each other and parallel to a central axis of the tubular member 2. The length of the cut-out 7 may also be varied. Preferably, the length of the cut-out 7 is greater than the circumference of the tubular member 2.

Additionally, the depth of the cut-out 7 may be varied depending on the desired properties. The greater the depth and length of the cut-out 7, the more flexible the tubular member is. Preferably, the depth of the cut-out 7 is at least one-half the diameter of the tubular member 2.

It is also envisioned in the present invention that the side edges and end edges of the cut-out 7 may be varied with respect to one another. As shown in FIGS. 5 and 6, the hinge means 6 may be tapered from one end of the cut-out 7 to the other end. For example, the cut-out 7 may be larger at the first end 3 of the tubular member 2 and smaller at the second end 4. Thus, the two spaced-apart longitudinally extending side edges 10 of the wall of the tubular member 2 may lie in a plane which is non-parallel to the central axis of the tubular member 2, as shown in FIG. 5. FIG. 6 shows an arrangement wherein the side edges 10 have a greater degree of tapering than in FIG. 5.

FIG. 4 shows an arrangement wherein end edges 11 of the cut-out 7 are perpendicular to the central axis of the tubular member 2. FIGS. 5 and 6 show arrangements wherein end edges 12 are not perpendicular to the central axis of the tubular member 2. The end edges can be connected to the side edges by arcuate corner edges 13 in the wall of the tubular member 2.

In one embodiment according to the invention, the cut-out 7 is defined by the two circumferentially spaced-apart side edges 9 lying in one plane and the two axially spaced-apart end edges 11 lying in another plane, the planes being perpendicular to each other. It should be noted, however, that the shape and size of the cut-out 7 preferably allows the first end 3 to bend and be of sufficient rigidity so that it will not collapse during bending, insertion and withdrawal of the device 1.

As shown in FIGS. 2 and 3, the tubular member 2 can be provided with a protective outer member 14 or sheath which covers the portion of the tubular member 2 at the location of the cut-out 7. The outer member 14 reduces resistance to movement which might be caused by the cut-out 7 and/or possible discomfort to the patient during insertion and withdrawal of the device. The outer member 14 also prevents materials from entering the side of the device through the cut-out 7 which could adversely affect the operation of a medical implement mounted in the tubular member 2. The outer member 14 may be constructed of various materials which are suitable for this application. Preferably the outer member is composed of a plastic material. Additionally, the outer member 14 may extend the entire length of the tubular member 2 as long as the cut-out 7 is covered. If desired, the outer member can also be used to cover the articulating means 8 so as to prevent contact of the articulating means 8 with the patient.

As previously mentioned, the articulating means 8 extends along the length of the tubular member 2. Preferably, the articulating means 8 lies under the outer member 14 and on the side of the tubular member 2 wherein the hinge means 6 is located. In this way, the articulating means 8 is contained within the device 1 and is not able to come in contact with the patient or obstruct a medical implement mounted within or made part of the tubular member 2. The construction therefore provides a smooth uninterrupted path for the articulating means 8 and reduces resistance when the articulating means 8 is in operation.

Many different medical implements may be inserted into or attached to the device 1, such as optical devices, catheterization devices, tissue removal devices, cutting devices and other various surgical and diagnostic devices. The usefulness of the invention may be best described via a preferred embodiment such as, but not limited to, a cholangiography catheter 15 shown in FIGS. 2 and 3. As can be seen from FIG. 2, the catheter 15 extends through and beyond the distal end 3 of tubular member 2. The catheter 15 is flexible and can be bent by the device 1. The catheter 15 may include a central lumen, or lumens, which allow for the implement to deliver contrast fluid, for example. Additionally, a distal balloon 16 may be attached to the catheter 15 beyond the distal end 3 of the tubular member 2 for use in a cholangiographic procedure.

Thus, there has been shown and described an improved medical steering device which fulfills all of the objects and advantages sought therefor. It will become apparent to those skilled in the art, however, that many changes, modifications, alterations, and other uses and applications of the subject device are possible, and all such changes, modifications, alterations, and other uses and applications that do not depart from the spirit and scope of the invention are deemed to be covered by invention.

What is claimed is:

1. A medical uniplanar steering device comprising:
   a tubular member having first and second spaced-apart ends and a central opening extending axially between the first and second ends;
   hinge means for connecting the first end to the second end and permitting uniplanar bending of the first end back and forth in a plane towards and away from the second end, the hinge means comprising a cut-out in a wall of the tubular member; and
   articulating means for moving the first end in the plane towards the second end of the tubular member, the articulating means comprising a control wire located on a side of the tubular member opposite to a side of the tubular member in which the cut-out is located.

2. The device of claim 1, wherein the control wire is attached to the first end of the tubular member, the control wire extending along the tubular member and beyond the second end of the tubular member, the control wire causing the first end to bend towards the second end when tension is applied to the control wire.

3. The device of claim 1, wherein the control wire is located on an outer periphery of the tubular member.

4. The device of claim 1, wherein the tubular member has a circular cross section and the tubular member is substantially uniform in diameter from the first end to the second end.

5. The device of claim 1, wherein the tubular member comprises a stainless steel tube.

6. The device of claim 1, wherein the cut-out is located between the first and second ends, the cut-out being defined by a circumferential section of the tubular member which extends circumferentially generally no more than one-fourth of a distance around the tubular member.

7. The device of claim 1, wherein the cut-out extends a distance along the tubular member, the distance being greater than a distance around a circumference of the tubular member.

8. The device of claim 1, wherein the cut-out extends circumferentially more than halfway around the tubular member.

9. The device of claim 1, wherein the cut-out is defined by two spaced-apart longitudinally extending side edges of the wall, the side edges being parallel to each other and parallel to a central axis of the tubular member.

10. The device of claim 1, wherein the cut-out is defined by two spaced-apart longitudinally extending side edges of the wall, the side edges lying a plane which is non-parallel to a central axis of the tubular member.

11. The device of claim 1, wherein the cut-out is tapered and the cut-out is larger at an end thereof closest to the first end of the tubular member.

12. The device of claim 1, wherein the cut-out is defined by two axially spaced-apart end edges of the wall, the end edges lying in planes which are parallel to each other.

13. The device of claim 1, wherein the cut-out is defined by two circumferentially spaced-apart side edges of the wall and two axially spaced-apart end edges of the wall, the end edges being joined to the side edges by arcuate corner edges in the wall of the tubular member.

14. The device of claim 1, further comprising a medical device, the medical device having a distal end thereof extending beyond the first end of the tubular member, the distal end of the medical device being oriented in a desired direction lying in the plane by applying tension to the control wire.

15. The device of claim 1, further comprising a catheter within the tubular member, the catheter including a balloon at a distal end of the catheter extending beyond the first end of the tubular member.

16. The device of claim 1, further comprising an outer member surrounding the tubular member, the outer member completely covering the cut-out.

* * * * *